United States Patent [19]
Sirinyan et al.

[11] Patent Number: 6,036,970
[45] Date of Patent: Mar. 14, 2000

[54] RODENTICIDAL FOAMS

[75] Inventors: Kirkor Sirinyan, Bergisch Gladbach; Manfred-Heinrich Schütte, Dormagen; Gerhard Hesse, Odenthal-Blecher; Reiner Pospischil, Bergheim; Rainer Sonneck, Leverkusen; Hans-Jürgen Schnorbach, Monheim, all of Germany

[73] Assignee: Bayer Aktiengesellschaft, Leverkusen, Germany

[21] Appl. No.: 08/669,701

[22] Filed: Apr. 3, 1996

Related U.S. Application Data

[63] Continuation-in-part of application No. 08/568,038, Dec. 6, 1995.

[30] Foreign Application Priority Data

| Dec. 13, 1994 | [DE] | Germany | 44 44 261 |
| Oct. 13, 1995 | [TR] | Turkey | 1266-95 |
| Nov. 10, 1995 | [PH] | Philippines | 51685 |
| Nov. 16, 1995 | [CL] | Chile | 1766-95 |
| Nov. 21, 1995 | [AR] | Argentina | 334317 |
| Nov. 28, 1995 | [TH] | Thailand | 28947 |
| Nov. 30, 1995 | [EP] | European Pat. Off. | 95118834 |
| Dec. 6, 1995 | [AU] | Australia | 40268-95 |
| Dec. 11, 1995 | [EG] | Egypt | 1015-95 |
| Dec. 11, 1995 | [FI] | Finland | 955937 |
| Dec. 11, 1995 | [MX] | Mexico | 955191 |
| Dec. 11, 1995 | [NZ] | New Zealand | 280650 |
| Dec. 11, 1995 | [PL] | Poland | 311777 |
| Dec. 11, 1995 | [VE] | Venezuela | 2146-95 |
| Dec. 12, 1995 | [BR] | Brazil | 9505761 |
| Dec. 12, 1995 | [CZ] | Czech Rep. | 3279-95 |
| Dec. 12, 1995 | [NO] | Norway | 955021 |
| Dec. 12, 1995 | [SK] | Slovakia | 1554-95 |
| Dec. 12, 1995 | [ZA] | South Africa | 95-10543 |
| Dec. 13, 1995 | [HU] | Hungary | 9503559 |
| Feb. 5, 1996 | [EP] | European Pat. Off. | 96101591 |

[51] Int. Cl.[7] .................. A61K 31/785; A01N 25/34
[52] U.S. Cl. ............. 424/408; 424/407; 424/78.17; 424/78.18; 424/78.19; 424/78.2; 424/78.27; 424/486; 424/487; 424/488; 424/405; 424/84
[58] Field of Search .................. 548/218, 256; 252/301.27, 301.29; 424/304, 309, 313, 324, 331, 78.17, 78.18, 78.19, 78.2, 78.27, 407, 405, 486, 184, 487, 488; 514/520, 522, 532, 533, 534, 535, 539

[56] References Cited

U.S. PATENT DOCUMENTS

| 3,816,610 | 6/1974 | Lusby et al. | 424/17 |
| 3,966,755 | 6/1976 | Schlapter | 548/256 |
| 4,017,483 | 4/1977 | Meyer | 548/218 |
| 4,207,335 | 6/1980 | Buckle et al. | 424/304 |
| 4,554,155 | 11/1985 | Allan et al. | 424/22 |
| 4,647,581 | 3/1987 | Kolbl et al. | 514/475 |
| 4,836,939 | 6/1989 | Hendrickson | 252/3 |
| 4,868,206 | 9/1989 | Hobbs | 514/457 |
| 4,944,110 | 7/1990 | Sims | 43/124 |

FOREIGN PATENT DOCUMENTS 1053088  12/1966  United Kingdom .

OTHER PUBLICATIONS

Zeitschrift Für Angewandte Zoologie 80, vol. 2, 1994, pp. 131–139.

*Primary Examiner*—Jose' G. Dees
*Assistant Examiner*—Kathryne E. Shelborne
*Attorney, Agent, or Firm*—Joseph C. Gil; Godfried R. Akorli

[57] ABSTRACT

The present invention relates to rodenticidal foams based on hydrophilic polymers, of the following composition:

a) rodenticidal active compound, b) hydrophilic polymers having an average molecular weight of 2,000 to 60,000 (determined by means of gel permeation chromatography (GPC) from the series consisting of ling-chain polyurethanes, polyesters, polyester-polyols, polystyrenes, polybutadienes and maleic acid polymers, which are in each case modified in the polymer chain by carboxylic acid groups or amino groups, c) long-chain aliphatic $C_6$–$C_{22}$-fatty acids, such as palmitic acid, dodecanoic acid and stearic acid, or alkali metal, alkaline earth metal and ammonium salts thereof, d) and if appropriate further auxiliaries from the series consisting of dyestuffs, emulsifiers, solvents, perservatives, attractants and baits.

6 Claims, No Drawings

RODENTICIDAL FOAMS

This is a continuation-in-part of application Ser. No. 08/568,038, filed on Dec. 6, 1995, now pending.

The present invention relates to rodenticidal foams based on hydrophilic polymers.

It is known that indanedione derivatives and 4-hydroxycoumarins lower the prothrombin level of blood. In rodents, they lead to a high mortality owing to internal haemorrhages. For this reason, they are employed as rodenticidal agents (in this context cf., for example, DE-OS (German Published Specification) 2 506 769, JP-PS (Japanese Published Specification) 480 23 942; CH-PS (Swiss Published Specification) 481 580).

In many cases, the rodenticidal active compound is mixed with various agents which can be eaten by rodents, such as, for example, cereal, flour, sugar and oil, and with inorganic auxiliaries, such as, for example, talc powder, chalk powder and $TiO_2$ powder.

Baits prepared by this method have the disadvantage, however, that their attractive power to rodents decreases greatly with time. The decrease in the attractiveness is to be attributed to chemical breakdown of the active compound or of the agents which can be eaten.

It is known that the attractive power of baits is maintained by coating the active compound with polymers, such as, for example, ethylcellulose, ethoxylated polyarylphenols, polyoxyethylene glycols, hydroxypropylmethylcellulose and the like (cf. EP 0 317 260, DE 26 47 722 and CA 107 963). This method has the disadvantage that only the active compound and not the agents which can be eaten by rodents is thereby protected from ageing. For this reason, this method is unsuitable for maintaining the attractive power of baits.

It is furthermore known that the attractive power of baits to rodents is maintained by employing chemically stable, hydrogenated oils and fats as the carrier material (in this context cf. JP-OS (Japanese Published Specification) 620 30 161). As a rule, however, oils and fats which are completely hydrogenated or have a low double bond content have a lower attractive power to rodents.

For this reason, attempts have been made to develop flexible rodenticidal foams which are free from agents which are sensitive to oxidation. Such rodenticidal foams as a rule comprise aliphatic acids, such as stearic acid; neutral, anionic or cationic emulsifiers; and various waxes, water and active compounds (in this context cf., for example, GB-PS (British Published Specification) 1 053 088, GB-PS (British Published Specification) 1 274 442, SU-PS (Soviet Published Specification) 363 474).

However, these rodenticidal foams have the disadvantage that they have a low storage stability, and in particular a low stability to low temperatures and moisture. They collapse in the course of time to form a compact, highly viscous mass and lose their biological action.

For this reason, attempts have been made to develop storage-stable rigid rodenticidal foams based on polystyrenes, polyacrylates and two-component polyisocyanates (in this context cf., for example, JP-OS (Japanese Published Specification) 55 085 501, FR-PS (French Published Specification) 2 676 888 and U.S. Pat. No. 4,190, 734). These rigid rodenticidal foams are distinguished by stability to storage, low temperatures and moisture. However, they have the disadvantage that their preparation is expensive. Furthermore, their biological action is low in many cases.

The invention is therefore based on the object of developing a new rodenticidal foam system which is distinguished by storage stability, resistance to moisture and low temperatures, easy preparation and application and a good biological action.

The present invention relates to flexible rodenticidal foams which comprise the following components:

a) rodenticidal active compound; preferably in a concentration of 0.001 to 5% by weight, based on the weight of the total formulation;

b) hydrophilic polymers having an average molecular weight of 2,000 to 60,000 (determined by means of gel permeation chromatography (GPC) from the series consisting of long-chain polyurethanes, polyesters, polyester-polyols, polystyrenes, polybutadienes and maelic acid polymers, which are in each case modified in the polymer chain by carboxylic acid groups or amino groups; preferably in a concentration of 2.5 to 40% by weight, based on the weight of the total formulation;

c) long-chain aliphatic $C_6$–$C_{22}$-fatty acids, such as palmitic acid, dodecanoic acid and stearic acid, or alkali metal, alkaline earth metal and ammonium salts thereof; preferably in a concentration of 2.5 to 20, particularly preferably of 2.5 to 12.5% by weight, based on the weight of the total formulation;

d) and, if appropriate, further auxiliaries from the series consisting of dyestuffs, emulsifiers, solvents, preservatives, attractants and baits; in a concentration of 0 to 15% by weight, based on the weight of the total formulation.

The polymers used according to the invention are described as paint binders, for example, in H. Kittel, Lehrbuch der Lacke und Beschichtungen [Textbook of Paints and Coatings], Volume IV, pages 76 to 306, Verlag W. A. Colomb (1986) or in the same textbook, Edition (1976), Volume IV, pages 328 to 358.

Polymers which can be used according to the invention are physically drying binders, for example those in which the binders are based on a completely reacted linear polyurethane of (i) a polyester-polyol, (ii) a chain lengthening agent and (iii) a diisocyanate and (iv) a hydroxycarboxylic acid.

Suitable polyester-polyols (i) for the preparation of such polyurethanes are, for example, adipic acid, alkanediol and polyester-diols of molecular weight range 600 to 3,000. The alkanediols are, for example, butane-1,4-diol, hexane-1,6-diol, neopentylglycol or mixtures of such glycols. Suitable chain lengthening agents (ii) are, for example, diols of the type employed for the preparation of the polyester-diols, and also diamines, such as hexamethylenediamine or isophoronediamine. Suitable diisocyanates (iii) are, for example, 4,4-diisocyanatodiphenylmethane, isophorone diisocyanate or hexamethylene diisocyanate. The polyurethanes are prepared by reaction of the starting materials in a manner known per se, a ratio of the equivalence of isocyanate groups to groups which are reactive towards isocyanate groups of about 0.9:1 to 1.1:1 being maintained.

Binders which dry by oxidation can also be used according to the invention. Such binders which may be mentioned are those based on polybutadiene, styrene and maleic anhydride and having ionic groups, such as are described in the Applications EP-A- 0 170 184 and EP-A 0 270 795.

The hydrophilic polymers which can be used according to the invention have an average molecular weight of 2,000 to 60,000 g/mol, preferably 2,500 to 25,000 g/mol. They are present in the finished formulation in a concentration of 2.5 to 40, preferably 2.5 to 10% by weight, based on the weight of the total formulation.

All rodenticidal active compounds are in principle suitable for preparation of the flexible rodenticidal foam according to the invention. Reference may be made in particular in this connection to the anticoagulating substances, such as the 4-hydroxycoumarin derivatives (1-phenyl-2-acetyl)-3-ethyl-4-hydroxycoumarin ("warfarin"), 3-(α-acetonyl-4-chlorobenzyl)-4-hydroxycoumarin ("coumachlor"), [3-(4'-hydroxy-3'-coumarinyl)-3-phenyl-1-(4'-bromo-4'-biphenyl)-propan-1-ol ("bromadiolone"), 3-(3'-paradiphenylyl-1',2',3',4'-tetrahydro-1'-naphthyl)-4-hydroxycoumarin ("difenacoum") brodifacoum, flocoumafen and 3-(1',2',3',4'-tetrahydro-1'-naphthyl)-4-hydroxycoumarin ("coumatetralyl"), the indanedione derivatives, such as 1,1-diphenyl-2-acetyl-indane-1,3-dione ("diphacinone") and (1'-p-chlorophenyl-1'-phenyl)-2-acetyl-indane-1,3-dione ("chlorodiphacinone") and the hydrocy-4-benzothiopyranones, for example difethialone.

The following 2-azacycloalkylmethyl-substituted benzhydryl ketones and carbinols may be mentioned as further anticoagulants which are suitable for preparation of the baits according to the invention: 1-phenyl-3-(2-piperidyl)-1-(p-tolyl)-2-propanone, 3,3-diphenyl-1-(2-pyrrolidinyl)-2-pentanone, 1,1-diphenyl-3-[2-(hexahydro-1H-azepinyl)]-2-propanone, 1-(4-fluorophenyl-1-phenyl-3-(2-piperidyl)-2-propanone, 1-(4-methylthiophenyl)-1-phenyl-3-(5,5-dimethyl-2-pyrrolidinyl)-2-propanone, 1-(p-cumenyl)-1phenyl-3-(4-tert-butyl-2-piperidinyl)-2-propanone, 3,3-diphenyl-1-[2-(hexahydro-1H-azepinyl]-2-butanone, 3-(2, 4-dichlorophenyl)-3-phenyl-1-(2-piperidyl)-2-heptanone,1, 1-diphenyl-3-(5-methyl-2-pyrrolidinyl)-2-propanones, 3,3-diphenyl-1-(2-piperidyl)-2-butanone, α-(α-methyl-α-phenylbenzyl)-2-piperidine-ethanol, α-(α-ethyl-α-phenylbenzyl)-2-pyrrolidine-ethanol, (2,5-dimethyl-α-phenylbenzyl)-2-piperidine-ethanol and α-(diphenylmethyl)-2-(hexahydro-1H-azepine)ethanol and their salts, which are described in DT-OS 2 417 783, and 4'-(fluorophenyl)-2-(2-pyrrolidinyl)-acetophenone, 4'-phenyl-2-(5,5-dimethyl-2-pyrrolidinyl)-acetophenone, 4'-[p-(trifluoromethyl)-phenyl]-2-(2-piperidyl)-acetophenone, 4'-(p-butoxyphenyl)-2-(4-tert-butyl-2-piperidyl)-acetophenone, 2'-phenoxy-2-(2-piperidyl)-acetophenone,4'-(p-fluorophenoxy)-2-(5,5-dimethyl-2-pyrrolidinyl)-acetophenone, 4'-(p-chlorophenoxy)-2-(2-piperidyl)-acetophenone, 4'-[m(trifluoromethyl)-phenoxy]-2-(2-piperidyl)-acetophenone, 4'-(p-butoxyphenoxy)-2-(2-pyrrolidinyl)-acetophenone, 2-(2-piperidyl)-4'-(trans-p-tolylvinylene)-acetophenone, 2-(2-hexahydro-1H-azepinyl)-4'-(trans-styryl)-acetophenone, 4'-(m-methoxyphenylvinylene)-2-(2-pyrrolidinyl)-acetophenone, 2-(2-piperidyl)-4'-[(p-methylthio)-phenylvinylene]-acetophenone, 4'-(3-phenoxypropoxy)-2-(2-piperidyl)-acetophenone, 4'-(4-phenylbutyl)-2-(2-piperidyl)-acetophenone,4'-(α,α-dimethylbenzyl)-2-(piperidyl)-acetophenone,4'-phenethyl-2-(3,5-diethyl-2-piperidyl)-acetophenone, 4'-phenyl-2-(2-pyrrolidinyl)-acetophenone, α-[2-(2-phenyl-ethoxy)phenyl]-2-piperidine-ethanol, α-(p-phenoxyphenyl)-2-pyrrolidine-ethanol, α-4-(4-bromophenoxy)-phenyl]-6-methyl-2-piperidine-ethanol, α-(p-phenethyl)-phenyl-2-pyrrolidine-ethanol, α-p-bisphenyl-2-hexanehydro-1H-azepine-ethanol, α-[3-(4-phenoxybutoxy)-phenyl]-2-piperidine-ethanol and α-(4-benzyl)-phenyl-2-piperidine-ethanol and their salts, which are described in DT-OS 2 418 480.

Acute poisons can of course also be employed for preparation of the new flexible rodenticidal foam.

The following rare earth metal salts can likewise be used as an anticoagulant: dineodymium dihydroxybenzenedisulphonate (Acta physiol. Acad. Sci. Hungar. 24, 373), dineaodymium 3-sulphonato-pyridine-4-carboxylate and cerium(III) tris-(4-aminobenzenesulphonate).

The amount of anticoagulants can be varied widely in the range between 0.001 and 5% (per cent by weight, based on the total bait composition), amounts of between 0.01 and 1.0% being preferred.

Other active compounds, such as cholecalciferol and calciferol, can of course be added to the baits according to the invention in amounts of 0.001 to 1.0%.

The flexible foams according to the invention can of course be provided with auxiliaries from the group consisting of attractants, fragrances, flavourings, paraffin derivatives, hydrogenated fats and oils.

Attractants which may be mentioned are, inter alia, naturally occurring oils, such as soya oil, rapeseed oil, corn oil or olive oil, oleic acid esters, such as, for example, glycerides, and sorbitan acid esters and mixtures thereof. Sweeteners, such as sugar, maltose, sucrose or molasses, may furthermore be mentioned.

The rodenticidal systems prepared in this way are premixes. As a rule, they must be diluted with water in amounts of 0–80% before application.

The flexible foams according to the invention can be prepared in a manner known per se by stirring or shaking. Another possibility is in situ preparation by means of blowing agents during application.

Blowing agents which may be mentioned for preparation of the formulations according to the invention are $CO_2$, $N_2O$, lower alkanes, such as propane or n-butane, isobutane, halogen-containing lower alkanes and low-boiling ethers, such as dimethyl ether, and mixtures of the said blowing agents.

The foam according to the invention has an outstanding adhesion to the rodent coat. It is dimensionally stable for several weeks and has a good rodent activity. It is suitable for combating rodents such as rats, mice and the like, including at damp locations (for example canals, riverbanks).

The invention will be illustrated in more detail with the aid of the following embodiment examples, without limiting its scope.

EXAMPLE 1

| | | |
|---|---|---|
| 1. Coumatetralyl | | 0.07% |
| 2. Stearic acid | | 7.50% |
| 3. Triethanolamine | | 4.16% |
| 4. Polywax 1550 | | 2.50% |
| 5. NP 10, a nonionic emulsifier | | 1.00% |
| 6. Glycerol | | 8.00% |
| 7. Crystalline sugar | | 5.00% |
| 8. Bayhydrol VP-LS 2069 | | 10.00% |
| 9. Tap water | about | 54.27% |
| 10. Isobutane | | 7.50% |
| | | 100.00% = 250 g |

This formulation was introduced into Al cans (1,000 ml). Bayhydrol VP-LS 2069 is an aqueous polyester-polyurethane from Bayer AG, D-51368 Leverkusen. It comprises soya oil fatty acid, trimethylolpropane, hexanediol, adipic acid, isophthalic acid, dimethylolpropionic acid, hexamethyl diisocyanate, isophorone diisocyanate, neopenthylglycol and dimethylethanolamine.

This formulation leads to flexible foams which are distinguished by their long-term and low-temperature stability. The flexible foams thus prepared are stable to low temperatures at −4° C. for several weeks and have an outstanding biological action against rodents. They are very suitable for combating mice, rats and the like.

Determination of the Biological Action

*Rattus norvegicus* Wild Strain

The animals originate from traps in the open and are reared in the laboratory. Weight of the test animals employed in g: 230/285/234/342/325

Test Method

The test was carried out with brown rats (*Rattus norvegicus*) wild form (number: 5) in a small enclosure in accordance with Guideline 9-3.2 of the Federal Biological Institute. The enclosure comprised three chambers lying one behind the other. Each chamber had a floor area of $1m^2$. The individual chambers were connected to one another by holes (battery). One chamber, which served the rats as "living space", contained a nesting box with hay and cellulose for building nests. The middle chamber remained empty. The food and test agent were laid out in the third chamber. Drinking water was available ad libitum through the entire test period. After the rats had been removed from the rearing pens, they were allowed to acclimatize themselves to the new environment for 3 days. After this acclimatization, the rats were prefed with Altromin O (standard diet) for one day.

A foam carpet (diameter: 40×60 cm/height: 1 cm) was then laid out at the entrance to the 3rd chamber. Feeding was continued with Altromin O, and the amounts eaten were determined daily be reweighing.

Results

The results are shown in Tables 1 and 2.

TABLE 1

Reactions of brown rats to a rodenticide foam carpet between the living and feeding area

| | |
|---|---|
| Start of experiment | A semi-circular foam carpet (diameter: 60 × 40 cm/height: 1 cm) is laid out in the food basin in front of the entrance. |
| 1st day | The rats have formed 2 circular holes in the foam, with the aid of which they can cross the foam by jumping in order to reach the food. Some flakes of foam lie in the running basin. The rats have a clean coat. |
| 2nd day | The foam carpet is renewed |
| 2nd day | The rats have formed a passage through the foam through which they can reach the food without touching the foam. Some flakes of foam lie in the running basin. The test animals have a clean coat. |
| 3rd day | Same result as on the 2nd day. |
| 4th day | The 1st rat is dead; otherwise the result is the same as on the preceding day. |
| 5th day | The 2nd rat is dead. One animal has coordination problems. The remaining rats continue to cross the foam carpet. |
| 6th day | The 3rd rat has died and 1 animal has poisoning symptoms. |
| 7th day | The 4th rat is dead. The last living animal shows no poisoning symptoms. |
| 8th–11th day | On the 10th day, the 5th rat also shows poisoning symptoms. On the 11th day the animal is dead. |

TABLE 2

Food intake during the 11 test days (n = 5 brown rats)

| Test day | 1st feeding point g | 2nd feeding point g | Dead individuals (total) |
|---|---|---|---|
| 1 | 31.6 | 22.4 | 0 |
| 2 | 71.1 | 44.0 | 0 |
| 3 | 71.7 | 32.7 | 0 |
| 4 | 30.9 | 21.4 | 1 |
| 5 | 0.0 | 2.9 | 2 |
| 6 | 2.8 | 0.0 | 3 |
| 7 | 2.3 | 2.9 | 4 |
| 8 | 4.0 | 0.0 | 4 |
| 9 | 3.0 | 0.0 | 4 |
| 10 | 0.0 | 3.1 | 4 |
| 11 | 0.0 | 0.0 | 5 |

The foam carpet between the living and feeding area necessarily had to be run through by the animals in order to reach the food. The animals formed a narrow path through the foam. Flakes of foam which remained attached to the coat were either scraped off in the middle basin or removed from the coat by grooming.

The time before the animals were filled (4–7 days) corresponds to our experiences with the "multible dose anticoagulant coumatetralyl".

One animal showed no poisoning symptoms until the 9th day and died only on the 11th day. It is to be assumed that this animal only crossed the foam carpet in the first nights after the other animals of the pack had already formed a lane through which it was possible to cross through the foam carpet without contamination.

EXAMPLE 2

| | |
|---|---|
| 1. Coumatetrolyl | 0.07% |
| 2. Stearic acid | 7.50% |
| 3. Triethanolamine | 4.16% |
| 4. Polywax 1550 | 2.50% |
| 5. NP10 | 1.00% |
| 6. Glycerol | 8.00% |
| 7. Crystalline sugar | 5.00% |
| 8. Bayhydrol VP-LS 2845 | 10.00% |
| 9. Tap water | 54.27% |
| 10. Isobutane/propane (1:1) | 7.50% |
| | 100.0% = 250 g |

This formulation was introduced into 1,000 ml cans. Bayhydrol VP-LS 2845 is an aqueous polyester-polyurethane solution from Bayer AG D-51368 Leverkusen. The polyurethane component comprises soya oil fatty acid, trimethylolpropane, hexanediol, adipic acid, isophthalic acid, dimethylolpropionic acid, isophorone diisocyanate and dimethylethanolamine. This formulation leads to flexible foams which are distinguished by their long-term and low-temperature stability. The flexible foams thus prepared are stable to low temperatures at 14° C. for several weeks and have an outstanding biological activity.

EXAMPLE 3

| | | |
|---|---|---|
| 1. Coumatetrolyl | 0.07% |
| 2. Stearic acid | 7.50% |
| 3. Triethanolamine | 4.16% |
| 4. Polywax 1550 | 2.50% |
| 5. NP 10 | 1.00% |
| 6. Glycerol | 8.00% |
| 7. Ctystalline sugar | 5.00% |
| 8. Bayhydrol B 130 | 10.00% |
| 9. Tap water | 54.27% |
| 10. Isobutane | 7.50% |

Bayhydrol B 130 is an aqueous polymer solution from Bayer AG. The polymer component comprises maleic anhydride, styrene, polybutadiene and ammonia.

This formulation leads to flexible foams which are distinguished by their long-term and low-temperature stability. The flexible foams thus prepared are stable to low temperatures at +4° C. for several weeks and have an outstanding biological action against rodents, such as mice and rats.

We claim:

1. Flexible rodenticidal foams which comprise the following components:
   a) rodenticidal active compound,
   b) hydrophilic polymers having an average molecular weight of 2,000 to 60,000 determined by means of gel permeation chromatography GPC from the group consisting of long-chain polyurethanes, polyesters, polyesters-polyols, polystyrenes, polybutadienes and maleic acid polymers, which are in each case modified in the polymer chain by carboxylic acid groups or amino groups,
   c) long-chain aliphatic $C_6$–$C_{22}$-fatty acids, or alkali metal, alkaline earth metal or ammonium salts of said fatty acids,
   d) and optionally further auxiliaries selected from the group consisting of dyestuffs, emulsifiers, solvents, preservatives, attractants and baits,
said components a)–d) being in admixture and in the form of flexible foam.

2. Premixes for the preparation of flexible rodenticidal foams comprising:
   a) rodenticidal active compound,
   b) hydrophilic polymers having an average molecular weight of 2,000 to 60,000 determined by means of gel permeation chromatography GPC from the group consisting of long-chain polyurethanes, polyesters, polyesters-polyols, polystyrenes, polybutadienes and maleic acid polymers, which are in each case modified in the polymer chain by carboxylic acid groups or amino groups,
   c) long-chain aliphatic $C_6$–$C_{22}$-fatty acids, or alkali metal, alkaline earth metal or ammonium salts of said fatty acids,
   d) and optionally further auxiliaries selected from the group consisting of dyestuffs, emulsifiers, solvents, preservatives, attractants and baits,
said premix being capable of forming a flexible foam.

3. Premixes according to claim 2, wherein the rodenticidal active compound is dissolved, dispersed, emulsified or suspended in a solution comprising the polymer, fatty acid or salt and if appropriate further auxiliaries.

4. Process for the preparation of flexible rodenticidal foams from premixes according to claim 2 comprising adding water to said premixes in amounts of 0 to 80% and foaming said premixes by stirring, shaking or in situ by means of blowing agents during application.

5. Premixes according to claim 3, wherein said long-chain fatty acids are selected from the group consisting of palmitic acid, dodecanoic acid, stearic acid, and alkali metal, alkaline earth metal and ammonium salts of palmitic acid, dodecanoic acid, and stearic acid.

6. A method of combating rodents comprising applying to an area where rodents are expected to trek a rodenticidally effective amount of a flexible rodenticidal foam according to claim 1.

* * * * *